US008623852B2

(12) United States Patent
Lambert et al.

(10) Patent No.: US 8,623,852 B2
(45) Date of Patent: Jan. 7, 2014

(54) TOPICAL METHODS AND COMPOSITIONS FOR THE TREATMENT OF EYE DISEASES AND CONDITIONS

(75) Inventors: Gregory Lambert, Chatenay Malabry (FR); Laura Rabinovich, Kadima (IL); Frederic Lallemand, Fresnes (FR); Betty Philips, Antony (FR)

(73) Assignee: Santen SAS, Evry (FR)

( * ) Notice: Subject to any disclaimer, the term of this patent is extended or adjusted under 35 U.S.C. 154(b) by 315 days.

(21) Appl. No.: 12/746,196

(22) PCT Filed: Dec. 3, 2008

(86) PCT No.: PCT/EP2008/066731
§ 371 (c)(1), (2), (4) Date: Jun. 4, 2010

(87) PCT Pub. No.: WO2009/071594
PCT Pub. Date: Jun. 11, 2009

(65) Prior Publication Data

US 2010/0286065 A1 Nov. 11, 2010

Related U.S. Application Data

(60) Provisional application No. 60/992,160, filed on Dec. 4, 2007.

(51) Int. Cl.
*A61K 31/56* (2006.01)
*A01N 45/00* (2006.01)

(52) U.S. Cl.
USPC ............................ 514/180; 514/169; 514/171

(58) Field of Classification Search
USPC .......................................... 514/180, 169, 171
See application file for complete search history.

(56) References Cited

U.S. PATENT DOCUMENTS

| | | | | |
|---|---|---|---|---|
| 4,340,594 A | | 7/1982 | Mizushima et al. | |
| 5,591,426 A | * | 1/1997 | Dabrowski et al. | ........ 424/78.04 |

FOREIGN PATENT DOCUMENTS

| | | | | |
|---|---|---|---|---|
| AU | 531 588 B | | 9/1983 | |
| EP | 1 864 667 A1 | | 12/2007 | |
| WO | 99/11270 A1 | | 3/1999 | |
| WO | WO99/11270 | * | 3/1999 | ............. A61K 31/57 |
| WO | 2007/138113 A1 | | 12/2007 | |

OTHER PUBLICATIONS

H. Benameur, et al, Liposome-incorporated Dexamethasone Palmitate Inhibits In-Vitro Lymphocyte Response to Mitogen, 47 J Pharm. Pharmacol. 812 (1995).*

Shunnugaperumal Tamilvanan & Simon Benita, The Potential of Lipid Emulsion for Ocular Delivery of Lipophilic Drugs, 58 Eur. J Pharma. Biopharma. 357 (2004).*

F. Lallemand, et al, Cyclosporine A Delivery to the Eye: A Pharmaceutical Challenge, 56 Eur. J Pharma. Biopharma. 307, (2003).*

International Search Report, dated Mar. 30, 2009, from corresponding PCT application.

* cited by examiner

*Primary Examiner* — Sean Basquill
(74) *Attorney, Agent, or Firm* — Young & Thompson

(57) ABSTRACT

The present invention relates to a new therapeutic approach for the treatment of eye diseases or conditions that allows for the delivery of corticosteroids to the eye's surface but does not cause any of the usual side effects associated with topical administration of corticosteroids. More specifically, the present invention provides methods of treatment involving the administration of a corticosteroid prodrug, such as dexamethasone palmitate, to the surface of the eye. Also provided are pharmaceutical compositions and kits for carrying out such methods of treatment.

9 Claims, No Drawings

TOPICAL METHODS AND COMPOSITIONS FOR THE TREATMENT OF EYE DISEASES AND CONDITIONS

BACKGROUND OF THE INVENTION

In the past 50 years or so, corticosteroids have been used in a broad spectrum of inflammatory conditions of the eye. In fact, corticosteroids belong to the class of therapeutics the most frequently prescribed in ophthalmology. In particular, topical corticosteroids have revolutionized the practice of ophthalmology and ophthalmic care when it comes to preventing or treating ocular inflammation due to trauma, chemical, infective, allergic or other causes. The most commonly used corticosteroids for topical ocular administration are prednisolone, fluorometholone, dexamethasone, rimexolone, and medrysone.

Corticosteroids are synthetic drugs that mimic steroid hormones naturally produced by the body. These steroid hormones have a wide variety of actions and control functions and are involved in a number of important physiological systems including stress response, immune response, and regulation of inflammation, carbohydrate metabolism, protein catabolism and blood electrolyte levels. In addition to regulating inflammation, corticosteroids also have the ability to affect these other physiological systems, resulting in many potential risks and side effects.

As with most therapeutic drugs, the majority of side effects of corticosteroids are more pronounced with systemic therapy. However, they may occur with all routes of administration. For example, there are several potentially severe ocular side effects that can result from topical corticosteroid use. In particular, topical corticosteroid therapy can cause an increase in intra-ocular pressure (IOP). If IOP remains elevated for a length of time, glaucoma can occur with corresponding optic nerve damage and visual field loss. IOP elevation can generally be reversed by discontinuation of the treatment. Another potential side effect that can result from topical corticosteroid use is the development of posterior subcapsular cataracts, which can be visually debilitating and require surgical removal. Topical corticosteroid use can also lead to an increase in corneal thickness, mydriasis (an excessive dilation of the pupil) and ptosis (dropping of the upper eyelid).

Side effects of topical corticosteroid therapy are generally directly related to the dosage and duration of treatment and are more often observed with the use of potent corticosteroids, such as dexamethasone. These side effects are believed to result, at least in part, from penetration of the corticosteroid in internal ocular tissues, such as the aqueous humor. The effectiveness of topical corticosteroid therapy is thus severely limited by these unwanted effects since it is often administered for a shorter period of time than necessary, and/or utilizes a less potent agent than necessary.

Therefore, there is still a need in the art for improved approaches to eliminate or reduce side effects associated with topical administration of corticosteroids in the treatment of eye diseases or conditions.

SUMMARY OF THE INVENTION

The present invention provides an improved strategy for the delivery of corticosteroids to the eye that does not result in undesirable side effects generally observed in topical corticosteroid therapy. The inventive approach is particularly useful in the treatment of eye diseases and conditions affecting the surface of the eye, such as ocular inflammatory conditions.

In particular, the present invention provides methods and compositions that include topical ocular administration of a corticosteroid prodrug, i.e., a pharmaceutically inactive compound that is converted to and/or releases a pharmaceutically active corticosteroid via a chemical or physiological process at the eye surface. Preferred corticosteroid prodrugs according to the present invention are compounds that do not significantly penetrate into internal ocular tissues after delivery to the eye surface, in particular that do not traverse the stroma, thereby not reaching the aqueous humor. Systems of the present invention thus limit or reduce the risk of increase in IOP, formation of glaucoma, formation of cataracts, and other unwanted side effects that can result from the presence of corticosteroids inside the eye. Consequently, therapeutic methods according to the present invention do not suffer from the limitations generally associated with topical corticosteroid administration, in that they can be administered for longer periods of time and can employ prodrugs of any suitable corticosteroid including the most potent corticosteroids.

More specifically, in one aspect, the present invention provides pharmaceutical compositions of corticosteroid prodrugs that are formulated for topical administration to the eye. An inventive pharmaceutical composition generally comprises an effective amount of at least one corticosteroid prodrug, or a physiologically acceptable salt thereof, and at least one pharmaceutically acceptable carrier or excipient.

Corticosteroids that may be released from corticosteroid prodrugs may be any corticosteroid suitable for use in the treatment of an eye disease or condition, in particular inflammatory conditions of the eye. In certain embodiments, a prodrug may be converted to and/or release a corticosteroid selected from the group of prednisolone, fluorometholone, dexamethasone, rimexolone, medrysone, physiologically acceptable salts thereof, derivatives thereof, and any combinations thereof. In certain preferred embodiments, a prodrug is converted to and/or releases dexamethasone, a physiologically acceptable salt thereof or a derivative thereof. More preferably, a prodrug according to the present invention is converted to and/or releases dexamethasone.

In certain preferred embodiments of the present invention, release of a corticosteroid from a prodrug occurs via an enzymatic process at the surface of the eye. Thus, preferably, a corticosteroid prodrug comprises a chemical group or function that can be cleaved by an enzyme present at the eye surface. Such enzymes include any of a wide variety of enzymes including, but not limited to, esterases (e.g., pseudocholinesterase, acetylcholine esterase), oxidoreductases, transferases, lyases, isomerases, ligases, hydrolases, phosphatases, proteases and peptidases. In certain preferred embodiments, release of a corticosteroid from a prodrug occurs via the action of one or more esterases.

Preferred corticosteroid prodrugs are lipophilic derivatives of corticosteroids, in particular lipophilic derivatives of corticosteroids having a log P (partition coefficient) comprised between 1 and 12, preferably higher than or equal to 5 and lower than 12.

According to the present invention, the partition coefficient P of a compound is the ratio of concentration of said compound in water to the concentration in octanol, as the neutral molecule.

The logarithm of said ratio is called log P. It can be determined with a suitable HPLC method according to published procedures (Caron, J. C., and Shroot, B., *J. Pharm. Sci.,* 1984).

In particular, the present invention relates to the use of lipophilic long chain esters of corticosteroids. Lipophilic long chains may be selected from the group consisting of linear alkyls, linear alkenyls, branched alkyls, and branched alkenyls, wherein alkyl and alkenyl groups comprise 12, 14, 16, 18 or more than 18 carbon atoms. Preferably, the lipophilic long chains are selected among linear or branched alkyls comprising 12, 14, 16, 18 or more than 18 carbon atoms. In one embodiment, the lipophilic long chains are selected among linear alkyls comprising 12 or 14 carbon atoms.

In certain preferred embodiments, a pharmaceutical composition according to the present invention comprises an effective amount of dexamethasone palmitate, dexamethasone myristate, dexamethasone laurate or dexamethasone caprate.

Pharmaceutical compositions of the present invention are formulated using any pharmaceutically acceptable carriers or excipients suitable for topical administration to the eye surface. For example, an inventive pharmaceutical composition may be formulated in a solution containing polyethylene glycols, in an oily solution, in an anionic emulsion or in a cationic emulsion.

Pharmaceutical compositions of the present invention may optionally further comprise at least one additional pharmaceutically active substance, which can be selected, for example, from the group consisting of an analgesic, an anesthetic, a haemostatic agent, an antimicrobial agent, an antibacterial agent, an antiviral agent, an antifungal agent, an antibiotic, an anti-inflammatory agent, an antioxidant, an antiseptic agent, an antihistamine agent, an antipruritic agent, an antipyretic agent, an immunostimulating agent, a dermatological agent, a anti-cancer agent, and any combination thereof.

In another aspect, the present invention provides methods for the treatment of eye diseases and conditions, in particular eye diseases and conditions that affect the surface of the eye, such as inflammatory conditions. Such methods generally comprise a step of: topically administering to a subject's eye surface, an effective amount of a pharmaceutical composition of the invention.

In preferred embodiments, administering a pharmaceutical composition according to an inventive method of treatment results in insignificant penetration of the corticosteroid prodrug and/or released corticosteroid inside the eye.

Methods of the present invention may be used for the treatment of a wide variety of eye diseases or conditions, in particular eye diseases or conditions affecting the eye surface, such as ocular inflammatory conditions. Inflammatory conditions of the eye may have any of a wide variety of causes, including trauma (e.g., surgery, laser procedure, accidental mechanical action), and chemical, infective, allergic or other causes. Alternatively, inflammation of the eye may be a manifestation of an eye disease or condition, or a manifestation of a systemic disease or condition.

In certain embodiments, a method according to the present invention further comprises a step of administering to the subject an effective amount of a therapeutic agent. Administration of such a therapeutic agent may be performed prior to, concomitantly with, and/or following administration of the pharmaceutical composition of corticosteroid prodrug. The therapeutic agent may be administered systemically. Alternatively, the therapeutic agent may be administered topically, for example to the surface of the eye.

In certain embodiments, the therapeutic agent has a therapeutic or beneficial effect on the eye disease or condition being treated by the inventive method. In other embodiments, administration of the therapeutic agent causes ocular side effects such as inflammation of the eye. In such embodiments, the pharmaceutical composition is administered to prevent or reduce these side effects. This approach may be particularly useful in the case of cyclosporine, which is indicated for the topical treatment of dry eye and is associated with side effects such as blurred vision, eye burning or stinging, eye discharge, eye itching, excessive tearing, discomfort or pain in the eye, and swelling around the eye. Administration of a pharmaceutical composition of the present invention before (e.g., for 1 week before) administration of cyclosporine is expected to prevent or reduce the risk of side effects, since it has been shown that combined administration of cyclosporine and a corticosteroid improves tolerance to cyclosporine and reduces discomfort in the eye at least at the beginning of the combined treatment.

These and other objects, advantages and features of the present invention will become apparent to those of ordinary skill in the art having read the following description.

DEFINITIONS

For purpose of convenience, definitions of a variety of terms used throughout the specification are presented below.

The term "corticosteroid", as used herein, refers to any of a wide variety of drugs that are closely related to cortisol, a hormone which is naturally produced in the adrenal cortex. Examples of corticosteroids include, but are not limited to, betamethasone, budenoside, cortisone, dexamethasone, hydrocortisone, methylprednisoline, prednisolone, prednisone, and triamcinolone. In certain preferred embodiments of the present invention, corticosteroids are effective in the treatment of an eye disease or condition via topical administration.

The term "prodrug" has herein its art understood meaning and refers to a pharmaceutically inactive compound that acts as a drug precursor which, following administration, is converted to and/or releases the pharmaceutically active drug. Conversion or release may occur via a chemical or physiological process (e.g., upon being brought to a physiological pH or through enzyme activity). Conversion or release may occur prior to, during, or following absorption, or at a specific target site of the body.

As used herein, the term "corticosteroid prodrug" refers to a prodrug which is metabolized in vivo and converted to and/or releases a pharmaceutically active corticosteroid by chemical or physiological process.

The term "lipophilic", when used herein to characterize a compound, refers to a compound that dissolves more readily in fats, oils, lipids, and non-polar solvents than in water.

As used herein, the term "lipophilic long-chain ester of a corticosteroid" refers to a chemical entity comprising an ester function, —COO—, wherein one of the carbon and oxygen atoms is covalently attached to a linear or branched alkyl or alkenyl chain comprising more than 10 carbon atoms, such as 12 carbon atoms, 14 carbon atoms, 16 or more, and wherein the other of the carbon and oxygen atoms is covalently attached to a functional group of the corticosteroid moiety.

The term "alkyl" has herein its art understood meaning and refers to a linear or branched saturated hydrocarbon.

The term "alkenyl" has herein its art understood meaning and refers to a linear or branched unsaturated hydrocarbon.

The terms "subject" and "individual" are used herein interchangeably. They refer to a human or another mammal (e.g., mouse, rat, rabbit, dog, cat, cattle, swine, sheep, horse or primate) that can be afflicted with or is susceptible to an eye disease or condition but may or may not have the disease or condition. In many embodiments, the subject is a human being. The terms "individual" and "subject" do not denote a particular age, and thus encompass adults, children, and newborns.

The term "eye disease or condition" refers to any of a wide variety of ocular conditions such as glaucoma, ocular inflammatory conditions such as keratitis, uveitis, ocular inflammation, allergy and dry eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), retinal diseases associated with glial proliferation, and the like.

The term "treatment" is used herein to characterize a method or process that is aimed at (1) delaying or preventing the onset of a disease or condition (in particular an eye disease or condition); (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

A "pharmaceutical composition" is defined herein as comprising an effective amount of a corticosteroid prodrug, or physiologically acceptable salt thereof, and at least one pharmaceutically acceptable carrier or medium.

As used herein, the term "effective amount", refers to any amount of a compound, agent or composition that is sufficient to fulfill its intended purpose(s), e.g., a desired biological or medicinal response in a tissue, system or subject. For example, in certain embodiments of the present invention, the purpose(s) may be: to slow down or stop the progression, aggravation, or deterioration of the symptoms of an eye disease or condition, to bring about amelioration of the symptoms of the disease or condition, and/or to cure the disease or condition. Determination of an effective amount is well within the ordinary skill in the art of pharmaceutical sciences and medicine, in that it may depend on various biological factors or individual variations and response to treatments.

The term "pharmaceutically acceptable carrier or excipient" refers to a carrier medium which does not interfere with the effectiveness of the biological activity of the active ingredient(s) and which is not excessively toxic to the host at a concentration at which it is administered. The term includes solvents, dispersion media, antibacterial and antifungal agents, isotonic agents, adsorption delaying agents, and the like. The use of such media and agents for pharmaceutically active substances is well known in the art (see, for example, "*Remington's Pharmaceutical Sciences*", E. W. Martin, 18$^{th}$ Ed., 1990, Mack Publishing Co.: Easton, Pa., which is incorporated herein by reference in its entirety).

The terms "therapeutic agent", "drug", and "pharmaceutically active substance" are used herein interchangeably. They refer to a substance, molecule, compound, agent, factor or composition effective in the treatment of a disease or condition.

The terms "approximately" and "about", as used herein in reference to a number, generally includes numbers that fall within a range of 10% in either direction of the number (greater than or less than the number) unless otherwise stated or otherwise evident from the context (except where such a number would exceed a possible value).

As used herein, the term "physiologically tolerable salt" refers to any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the like. Base addition salts can be formed with inorganic bases (e.g., sodium, potassium, lithium, ammonium, calcium, magnesium, zinc, aluminium salts, and the like) and organic bases (e.g., salts of primary, secondary and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexylamine, lysine, arginine, histidine, caffeine, procaine, hydrabanine, choline, betaine, ethylene-diamine, glycosamine, methylglucamine, theobromine, purines, piperazine, N-ethylpiperidine, polyamine resins, and the like).

The term "topical formulation" and "topical composition" are used herein interchangeably. They refer to a composition formulated such that the active ingredient(s) of the composition may be applied for direct administration to the surface of the eye and from which an effective amount of the active ingredient(s) is released. Examples of topical formulations include, but are not limited to, lotions, sprays, ointments, creams, gels, pastes, and the like.

The term "topical", when used herein to characterize the delivery, administration or application of a composition of the present invention, is meant to specify that the composition is delivered, administered or applied directly to the site of interest (i.e., to the eye) for a localized effect. Preferably, topical administration is effected without any significant absorption of components of the composition into the subject's blood stream (to avoid a systemic effect). In certain preferred embodiments of the present invention, topical administration of a composition is effected without any significant absorption of components of the composition into the subject's eye tissues, such as the aqueous humor, and corneal and conjunctival tissues.

The term "non-invasive", when used herein refers to a method or mode of administration that does not rupture or puncture (e.g., by a mechanical means) of a biological membrane to which a corticosteroid prodrug is being delivered.

The term "ophthalmic", as used herein in connection with a composition, refers to a composition intended to be administered to the eye and which presents a pharmaceutical effect.

DETAILED DESCRIPTION OF CERTAIN PREFERRED EMBODIMENTS

As mentioned above, the present invention relates to topical administration of a corticosteroid prodrug to the surface of the eye for the treatment of eye diseases or conditions. The therapeutic strategy provided by the present invention has the advantage of eliminating undesirable side effects that are generally associated with topical corticosteroid administration.

I—Corticosteroid Prodrugs

Corticosteroid prodrugs suitable for use in the practice of the present invention include any molecule which is converted to and/or releases a corticosteroid via a chemical or physiological process following topical administration to the surface of the eye.

Examples of corticosteroids that can be released by a corticosteroid prodrug according to the present invention include, but are not limited to, alclometasone, amcinonide, amcinafel, amcinafide, beclamethasone, betamethasone, clobetasone, chloroprednisone, clocortelone, cortisol, C21-desmethylpropionyl-ciclesonide, cortodoxone, difluorosone, descinolone, desonide, defluprednate, dihydroxycortisone, desoximetasone, dexamethasone, deflazacort, diflorasone, dichlorisone, fluazacort, flucetonide, flucloronide, fludrotisone, fluorocortisone, flumethasone, flunisolide, fluocinonide, fluocinolone, flucortolone, fluperolone, fluprednisolone, fluroandrenolone, flurandrenolide, fluorametholone, fluticasone, hydrocortisone, hydrocortamate, loteprendol, medrysone, meprednisone, methylprednisone, methylprednisolone, mometasone, paramethasone, prednisolone, and triamcinolone, physiologically acceptable salts thereof, derivatives thereof, and any combinations thereof.

In certain embodiments, the corticosteroid released by a corticosteroid prodrug is selected from the group consisting of prednisolone, fluorometholone, dexamethasone, rimexolone, and medrysone, physiologically acceptable salts thereof, derivatives thereof, and any combinations thereof. In certain preferred embodiments, the corticosteroid is dexamethasone, a physiologically acceptable salt thereof, or a derivative thereof.

In certain embodiments, a corticosteroid prodrug according to the present invention comprises a lipophilic derivative of a corticosteroid. Lipophilic derivatives generally exhibit low diffusion coefficients, and consequently are less likely to be transported inside the eye, thus limiting penetration of the prodrug and consequent release of the corticosteroid in internal ocular tissues, where it can induce formation of glaucoma, cataracts, and other unwanted physiological alterations. The use of lipophilic derivatives of corticosteroids as prodrugs thus eliminates or, at least reduces, the risks of unwanted side effects.

Preferably, the composition of the present invention contains an effective amount of a lipophilic derivative of a corticosteroid having a log P comprised between 1 and 12. More preferably the log P of said lipophilic derivative of corticosteroid is higher than or equal to 5 and lower than 12 ($5 \leq \log P < 12$).

In one embodiment, the log P of said lipophilic derivative of corticosteroid is comprised between 6 and 11.

In another embodiment, the log P of said lipophilic derivative of corticosteroid is comprised between 7 and 10.

In another embodiment, the log P of said lipophilic derivative of corticosteroid is comprised between 8 and 9.

In one embodiment, the log P of said lipophilic derivative of corticosteroid is comprised between 5 and 6.

In another embodiment, the log P of said lipophilic derivative of corticosteroid is comprised between 6 and 8.

In another embodiment, the log P of said lipophilic derivative of corticosteroid is comprised between 7 and 11, or between 8 and 10.

In another embodiment, the log P of said lipophilic derivative of corticosteroid is comprised between 9 and 11.

Preferably, release of the corticosteroid by a lipophilic derivative occurs via a physiological process, such as an enzymatic cleavage, at the surface of the eye. Thus, in certain preferred embodiments, a lipophilic derivative of a corticosteroid comprises a chemical group that can be cleaved by an enzymatic process. According to the present invention, the inactive corticosteroid prodrug is converted into an active corticosteroid at the surface of the eye, by an enzyme present at the surface of the eye.

For example, a lipophilic derivative may comprise an ester that is cleavable by the action of an enzyme belonging to the family of esterases, e.g., pseudocholinesterase or acetylcholine esterase.

Other examples of enzymes that can catalyze the cleavage of corticosteroid prodrugs of the present invention include, but are not limited to:

Oxidoreductases acting on the CH, $CH_2$, CH—OH, aldehyde, oxo, CH—CH, CH—$NH_2$, CH—NH, sulfur, phosphorus, arsenic or heme groups of donors; oxidoreductases acting on NADH or NADPH; oxidoreductases acting on nitrogenous compounds, diphenols and related substances or hydrogen as donors; oxygenases; oxidoreductases acting on peroxide or superoxide radicals as acceptors; oxidoreductases acting on the iron-sulfur proteins as donors;

Transferases transferring one carbon, alkyl, aryl, nitrogenous, aldehyde or ketone groups; transferases; acyltransferases; glycosyltransferases; transferases transferring phosphorus-, selenium- or sulfur-containing groups;

Lyases such as carbon-carbon, carbon-oxygen, carbon-nitrogen, carbon-sulfur, carbon-halide or phosphorus-oxygen lyases;

Isomerases such as racemases and epimerases; oxidoreductases; intramolecular transferases or intramolecular lyases; and Ligases forming carbon-oxygen, carbon-sulfur, carbon-nitrogen, carbon-carbon, phosphoric ester or nitrogen-metal bonds.

Preferred enzymes are hydrolases which act on ester or ether bonds, hydrolases acting on carbon-nitrogen, carbon-carbon, halide, phosphorus-nitrogen, sulfur-nitrogen, carbon-phosphorus, sulfur-sulfur or carbon-sulfur bonds; glycosylases; peptidases; hydrolases acting on acid anhydrides.

More preferred enzymes are esterases.

Thus, in certain preferred embodiments, a corticosteroid prodrug of the present invention comprises an ester group. More preferably, a corticosteroid prodrug comprises a lipophilic long-chain ester of a corticosteroid. Preferred lipophilic long-chain esters of corticosteroids comprise an ester function and have one of the following formula: LLC-COO—R or R—COO-LLC, wherein LLC is a lipophilic long chain and R is a corticosteroid moiety. LLC may be any suitable lipophilic long chain. For example, LLC may be a long linear or branched alkyl or alkenyl chain, e.g., a C4-C16 alkyl chain or a C12, C14, C16, C18 or C20 saturated or unsaturated alkenyl chain.

In certain embodiments, the corticosteroid prodrug is dexamethasone palmitate. Dexamethasone palmitate has a very low diffusion coefficient, and thus does not significantly penetrate inside the eye following topical administration (C. Civiale et al., J. Ocul. Pharm. Ther., 2004, 20: 75-84).

Covalent binding of the lipophilic long chain and corticosteroid moiety through an enzyme-cleavable chemical group can be achieved by taking advantage of reactive functional groups present on the lipophilic long chain and/or corticosteroid molecule. Alternatively or additionally, reactive functional groups may be added to the lipophilic long chain and/or corticosteroid molecule. Reactive functional groups may be selected from a wide variety of chemical groups including, but not limited to, haloformyl, hydroxyl, aldehyde, alkyl, alkenyl, alkynyl, carboxamide, primary amine, secondary amine, tertiary amine, quaternary ammonium ion, azo (Diimide), benzyl, carboxylate, carboxyl, cyanate, thiocyanate, ether, ester, halo, primary ketimine, secondary ketimine, primary aldimine, secondary aldimine, isocyanide, isocyanate, isothiocyanate, ketone, nitrile, nitro, nitroso, peroxy, phenyl, phosphino, phosphate, phosphono, phosphate, pyridyl, sulfonyl, sulfo, sulfinyl or sulfhydryl groups. Methods to introduce each of these functional groups are well known in the art and their application to or modification for a particular purpose is within the ability of one of skill in the art (see, for example, Sandler and Karo, Eds., "*Organic Functional Group Preparations*", Academic Press: San Diego, 1989). Reactive functional groups may be protected or unprotected.

Corticosteroid prodrugs of the present invention may be synthesized using methods and procedures known in the art or may be purchased from commercial sources and optionally purified before formulation and/or administration.

II—Topical Compositions of Corticosteroid Prodrugs

Corticosteroid prodrugs described herein may be administered per se or in the form of a pharmaceutical composition. Accordingly, the present invention provides pharmaceutical compositions comprising an effective amount of at least one corticosteroid prodrug described herein and at least one pharmaceutically acceptable carrier, vehicle or excipient. In preferred embodiments, pharmaceutical compositions are formulated for topical administration, in particular, topical administration to the surface of the eye.

Pharmaceutical compositions of the present invention may be in the form of liquid or semi-solid dosage preparations. For example, inventive corticosteroid prodrug compositions may be formulated as solutions, dispersions, suspensions, emulsions, mixtures, lotions, liniments, jellies, ointments, creams, pastes, gels, hydrogels, aerosols, sprays, foams, and the like. In certain preferred embodiments of the present invention, compositions are formulated as lipophilic solutions, anionic emulsions or cationic emulsions.

The inventive topical compositions may be prepared according to general pharmaceutical practice (see, for example, "*Remington's Pharmaceutical Sciences*", E. W. Martin, 18$^{th}$ Ed., 1990, Mack Publishing Co.: Easton, Pa. and "*Encyclopedia of Pharmaceutical Technology*", 1988, J. Swarbrick, and J. C. Boylan (Eds.), Marcel Dekker, Inc: New York, each of which is incorporated herein by reference in its entirety).

Pharmaceutically acceptable carriers, vehicles, and/or excipients suitable for incorporation into topical compositions of the present invention can be routinely selected for a particular use by those skilled in the art. Such carriers, vehicles and excipients include, but are not limited to, solvents, buffering agents, inert diluents, suspending agents, dispersing agents or wetting agents, preservatives, stabilizers, chelating agents, emulsifying agents, anti-foaming agents, gel-forming agents, humectants, and the like. Excipient characteristics that are considered include, but are not limited to, the biocompatibility and biodegradability at the site of administration, compatibility with the prodrug of interest, and processing temperatures.

Examples of solvents are water or purified water; alcohols (e.g., ethanol, benzyl alcohol), vegetable, marine and mineral oils, polyethylene glycols, propylene glycols, glycerol, and liquid polyalkylsiloxanes, and combinations thereof.

In certain preferred embodiments, pharmaceutical compositions of the present invention are formulated as solutions comprising polyethylene glycol(s).

In other preferred embodiments, pharmaceutical compositions of the present invention are formulated using one or more oily carriers. Examples of suitable oily carriers include, but are not limited to, mineral oils such as silicone, paraffin or vegetal oils such as medium chain triglycerides, castor oil, olive oil, corn oil, soybean oil, palm oil or any other oil suitable for topical administration. For example, the weight ratio prodrug/oil in an inventive composition may be between about 0.04 and about 0.3.

In still other embodiments, pharmaceutical compositions of the present invention are formulated as oil-in-water or water-in-oil emulsions. Preferably, the emulsion is an oil-in-water emulsion. The emulsion may be anionic or cationic.

In embodiments where the carrier is an anionic emulsion, it may be preferred that said emulsion comprises colloid particles having an oily core surrounded by interfacial film, the film comprising surface active agents, lipids or both, at least part of the surface active agents or lipids in the interfacial film having negatively charged polar groups, and the colloid particles have a negative zeta potential. Preferably, the prodrug is comprised within the emulsion in an amount of about 0.01% to about 10% w/w of the composition, e.g., about 0.5% to about 3% w/w, for example about 2% w/w or about 1% w/w. The oil phase may represent at least about 1, at least about 5, at least about 10, at least about 20, at least about 30 or at least about 40 weight percent of the composition. For example, in certain preferred embodiments, the oil represents between 0.5 and 5% weight percent of the composition. In such embodiments, the composition may include at least one surfactant, preferably in an amount of about 0.1% to about 10% w/w of the composition. The surfactant may be selected from phospholipids, poloxamers, tyloxapol, polysorbate, and polyexyethylene fatty acid esters. An isotonicity agent, e.g., glycerol, may be present in the composition in an amount of about 0.1% to about 10% w/w of the composition.

In embodiments where the carrier is a cationic emulsion, it may be preferred that said emulsion comprises colloid particles having an oily core surrounded by interfacial film, the film comprising surface active agents, lipids or both, at least part or the surface active agents or lipids in the interfacial film having positively charged polar groups, and the colloid particles have a positive zeta potential. Such emulsions may be similar to those described above, with surfactants being selected from cationic surfactants, such as quaternary ammonium compounds, such as cetalkonium chloride.

As already mentioned above, other excipients that can be present in compositions of the present invention include, but are not limited to, emulsifying agents, inert diluents, buffering agents, suspending agents, dispersing or wetting agents, preservatives, chelating agents, anti-foaming agents, gel bases or viscosity-increasing agents, and any combinations thereof.

Examples of emulsifying agents are naturally occurring gums, naturally occurring phosphatides (e.g., soybean lecithin, sorbitan mono-oleate derivatives), sorbitan esters, mono glycerides, fatty alcohols (e.g., cetyl alcohol, oleyl alcohol), and fatty acid esters (e.g., triglycerides of fatty acids, sodium cetostearyl sulfate).

Inert diluents may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, diethylamine, sodium hydroxide and tromethane (i.e., tris-(hydroxymethyl) aminomethane hydrochloride).

Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans.

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a topical composition of the invention to prevent microbial contamination that can affect the stability of the formulation and/or cause infection in the patient. Suitable examples of preservatives include parabens (such as methyl, ethyl, propyl, p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol.

Examples of chelating agents include sodium EDTA and citric acid.

Anti-foaming agents usually facilitate manufacture of pharmaceutical compositions, they dissipate foam by destabilizing the air-liquid interface and allow liquid to drain away from air pockets. Examples of anti-foaming agents include simethicone, dimethicone, ethanol, and ether.

Examples of gel bases or viscosity-increasing agents are liquid paraffin, polyethylene, fatty oils, colloidal silica or aluminum, glycerol, propylene glycol, propylene carbonate, carboxyvinyl polymers, magnesium-aluminum silicates, hydrophilic polymers (such as, for example, starch or cellulose derivatives), water-swellable hydrocolloids, carragenans, hyaluronates, alginates, and acrylates.

In certain embodiments of the present invention, topical compositions are formulated to provide a local controlled release of one or more components of the composition. Any pharmaceutically acceptable carrier vehicle or formulation suitable for local administration to the eye may be employed. Examples of slow release formulation include polymer formulations (such as vesicles or liposomes) and microparticles (such as microspheres or microcapsules).

A wide variety of biodegradable materials may be used to provide controlled release of one or more components of compositions of the present invention. The controlled release material should be biocompatible and be degraded, dissolved or absorbed in situ in a safe and pharmaceutically acceptable manner so that the material is removed from the site of administration by natural tissue processes and in a suitable amount of time. The controlled release carrier should not cause any unwanted local tissue reaction or induce systemic or local toxicity.

Suitable controlled release biodegradable polymers for use in the formulation of topical compositions of the invention may comprise polylactides, polyglycolides, poly(lactide-co-glycolides), polyanhydrides, polyorthoesters, polycaprolactones, polysaccharides, polyphosphazenes, proteinaceous polymers and their soluble derivatives (such as gelation biodegradable synthetic polypeptides, alkylated collagen, and alkylated elastin), soluble derivatives of polysaccharides, polypeptides, polyesters, and polyorthoesters.

The pharmacokinetic release profile of these formulations may be first order, zero order, bi- or multi-phasic, to provide the desired therapeutic effect over the desired period of time. A desired release profile can be achieved by using a mixture of polymers having different release rates and/or different percent loadings of corticosteroid prodrug, or a physiologically acceptable salt thereof. Methods for the manufacture of liposomes, microspheres and microcapsules are well known in the art.

In certain embodiments, topical compositions of the present invention further comprise at least one additional therapeutic agent. Suitable therapeutic agents include any drug whose topical administration to the surface of the eye is beneficial to the subject receiving the composition.

Suitable therapeutic agents may be found in a wide variety of classes of drugs including, but not limited to, analgesics, anesthetics, relaxants, hormones, anti-inflammatory agents, vitamins, minerals, anti-angiogenic agents, wound healing agents, cytokines, growth factors, anti-histaminic agents, anti-bacterial agents, anti-viral agents, antibiotics, antipruritic agents, antipyretic agents, and the like.

For example in certain embodiments, compositions of the present invention comprise one or more antiviral drugs. Suitable antiviral drugs include, but are not limited to, idoxuridine, trifluorothymidine, trifluorouridine, acyclovir, ganciclovir, cidofovir, interferon, DDI, AZT, foscamet, vidarabine, irbavirin, and the like.

In other embodiments, the additional therapeutic agent is selected from non-steroidal anti-inflammatory drugs. Examples of suitable non-steroidal anti-inflammatory drugs include, but are not limited to, amfenac, ketorolac, indomethacin, ibuprofen, diclofenac, flurbiprofen, piroxicam and other COX2 inhibitors; cytokines, interleukines and growth factors epidermal growth factor, fibroblast growth factor, pigment epithelium growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or proteins inhibiting the activity of such cytokines and growth factors.

In still other embodiments, the therapeutic agent comprises an anti-angiogenic drug. Examples of antiangiogenic drugs include, but are not limited to, anecortave, combretastatin, vascular endothelial growth factor (VEGF) inhibitors, squalamine, AdPEDF, VEGF-traps; immunological response modifiers chosen from the group comprising mycophenolic acid, muramyl dipeptide, cyclosporins, interferons, interleukin-2, cytokines, tacrolimus, tumor necrosis factor, pentostatin, thymopentin, transforming factor beta$_2$, erythropoetin; antineogenesis proteins; antibodies (monoclonal or polyclonal) or antibodies fragments, oligoaptamers, aptamers and gene fragments (oligonucleotides, plasmids, ribozymes, small interference RNA (SiRNA), nucleic acid fragments, peptides), and the like.

In yet other embodiments, the therapeutic agent may be selected among antibiotics (e.g., aminoglycosides, carbacephem, carbapenems, cephalosporins, glycopeptides, penicillins, polypeptides, quinolones, sulfonamides, tetracyclines and the like); antifungals (e.g., polyene antibiotics, imidazole and triazole, allylamines); intraocular pressure lowering agents (e.g., alpha-adrenergic agonists, beta-adrenergic blockers, carbonic anhydrase inhibitors, cannabinoids, derivatives and prodrugs); antiallergic compounds (e.g., olapatadine, ketotifen, azelastine, epinastine, emedastine, levocabastive, terfenadine, astemizole and loratadine); biological agents (e.g., antibodies or antibodies fragments, oligoaptamers, aptamers and gene fragments, oligonucleotides, plasmids, ribozymes, small interference RNA, nucleic acid fragments, peptides and antisense sequences); growth factors (e.g., epidermal growth factor, fibroblast growth factor, platelet derived growth factor, transforming growth factor beta, ciliary neurotrophic growth factor, glial derived neurotrophic factor, NGF, EPO and P1GF); immunomodulating agents (e.g., glucocorticoids, drugs acting on immunophilins, interferons, opioids); cytostatics (e.g., alkylating agents, antimetabolites and cytotoxic antibiotics); antioxidants (e.g., alpha-tocopherol, ascorbic acid, retinoic acid, lutein and their derivatives, precursors or prodrugs; UV-filter compounds (e.g., benzophenones); anti-redness agents (e.g., naphazoline, tetrahydrozoline, ephedrine and phenylephrine); fatty acids (e.g., omega-3 fatty acids), and the like, and any combination thereof.

Pharmaceutical compositions of the present invention may be formulated in dosage unit form for ease of administration and uniformity of dosage. The expression "unit dosage form", as used herein, refers to a physically discrete amount of a corticosteroid prodrug composition (optionally comprising pharmaceutically active substance(s)) to treat a patient. It will be understood, however, that the total daily using of compositions of the present invention will be decided by the attending physician within the scope of sound medical judgment.

In certain embodiments, compositions of the present invention are combined with, coated on, or incorporated within a device that can be applied to the eye, e.g., an ocular lens.

III—Indications and Administration

The pharmaceutical composition according to the present invention may be used in a method for treatment of the human or animal's eye.

In one aspect, the pharmaceutical composition according to the present invention may be used in a method for treatment of an ocular inflammatory condition through topical administration of said composition to the surface of said eye.

In another aspect, the pharmaceutical composition according to the present invention may be used for reducing side effects associated with topical administration of a corticosteroid, such as intra-ocular pressure.

In another aspect, the present invention relates to methods for the treatment of eye diseases or conditions, in particular to eye diseases or conditions affecting the surface of the eye. Such methods comprise a step of topically administering to a subject's eye surface an effective amount of a corticosteroid prodrug as described herein, or a pharmaceutical composition thereof. Said method results in insignificant penetration of the corticosteroid prodrug or corticosteroid or both in the eye.

Methods of the present invention are particularly useful in the treatment of eye inflammation conditions. Eye inflammation conditions may result from trauma (e.g., surgery, laser procedure, or accidental mechanical action), infection, allergy, chemical contact or other causes. Alternatively, eye inflammation may be one of the manifestations of an eye disease or condition. Eye inflammation may also be one of the manifestations of a systemic disease or disorder or may be associated with a systemic disease or disorder.

Eye diseases or conditions may be any of a wide variety of ocular conditions such as glaucoma, ocular inflammatory conditions such as keratitis, uveitis, intra-ocular inflammation, allergy and dry-eye syndrome ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), and retinal diseases associated with glial proliferation.

Examples of systemic diseases or disorders with ocular manifestations include, but are not limited to, acute posterior multifocal placoid pigment epitheliopathy, ankylosing spondylitis, Behçet's disease, Birdshot retinochoroidopathy, brucellosis, Herpes simplex, Herpes zoster, inflammatory bowel disease, juvenile rheumatoid arthritis, Kawasaki's disease, Leptospirosis, Lyme disease, multiple sclerosis, presumed ocular histoplasmosis syndrome, psoriatic arthritis, Reiter's syndrome, sarcoidosis, syphilis, systemic lupus erythematosus, toxocariasis, toxoplasmosis, tuberculosis, Vogt-Koyanagi-Harada syndrome, and Whipple disease.

A treatment according to the present invention may consist of a single dose or a plurality of doses over a period of time. Administration may be one or multiple times daily, weekly (or at some other multiple day interval) or on an intermittent schedule.

Optimization of the appropriate dosages can readily be made by one skilled in the art in light of pharmacokinetic data observed in clinical trials. Final dosage regimen will be determined by the attending physician, considering various factors which modify the action of the drug, e.g., the drug's specific activity, the severity of the disease or condition and the responsiveness of the patient, the age, condition, body weight, sex and diet of the patient, the severity of any present infection, time of administration, the use (or not) of concomitant therapies, and other clinical factors. As studies are conducted using compositions of the present invention, further information will emerge regarding the appropriate dosage levels and duration of treatment.

It will be appreciated that pharmaceutical compositions of the present invention can be employed alone or in combination with additional therapies. The method according to the present invention may further comprise a step of administering to the subject an effective amount of a therapeutic agent. This therapeutic agent may be administered prior to, concomitantly with, or following administration of the pharmaceutical composition of the corticosteroid prodrug. The particular combination of therapies (therapeutics or procedures) to employ in such combination regimen will take into account compatibility of the desired therapeutics and/or procedures and the desired therapeutic effect to be achieved.

For example, a pharmaceutical composition of the present invention may be administered to a subject following eye surgery. In such embodiments, administration of a corticosteroid prodrug may prevent or reduce post-surgical inflammation. Examples of eye surgery procedures include, but are not limited to, laser surgery; cataract surgery; glaucoma surgery (e.g., canaloplasty), refractive surgery (e.g., keratomilleusis, automated lamellar keratoplasty, Laser assisted in situ keratomileusis or LASIK, photorefractive keratectomy, laser thermal keratoplasty, conductive keratoplasty, and astigmatic keratotomy); corneal surgery (e.g., corneal transplant surgery, penetrating keratoplasty, and phototherapeutic keratectomy); vitréo-retinal surgery (e.g., vitrectomy, retinal detachment repair, and macular hole repair); eye muscle surgery; oculoplastic surgery; eyelid surgery; orbital surgery; and other ophthalmologic surgery procedures.

In another example, a pharmaceutical composition of the present invention may be administered to a subject receiving a drug, or a combination of drugs, that causes undesirable effects to the surface of the eye, e.g., inflammation, irritation, itching, redness, pain, and the like. These effects may result from systemic or local administration of the drug (or drug combination). In such embodiments, administration of an inventive pharmaceutical composition of corticosteroid prodrug may prevent or reduce these undesirable side effects.

Thus, pharmaceutical compositions of the present invention may be administered in combination with any of a wide variety of drugs that have undesirable effects to the surface of the eye. In certain embodiments, the pharmaceutical composition is administered concomitant with the drug (e.g., at the same time or on the same day). Alternatively or additionally, the pharmaceutical composition is administered prior to administration of the drug (e.g., days or weeks before) to prevent or reduce occurrence of unwanted side effects to the eye of the subject.

The therapeutic agent may be administered systemically or to the subject's eye surface.

The use of corticosteroid prodrugs for the prevention or reduction of undesirable effects caused by other drugs is, for example, particularly advantageous in the case of treatments involving cyclosporine. Cyclosporine is indicated for the treatment of dry eye to increase tear production (an ophthalimic emulsion of cyclosporine is commercially available under the trade name Restasis™ from Allergan, Inc.). Side effects associated with such treatment include blurred vision, eye burning or stinging, eye discharge, eye itching, excessive tearing, discomfort or pain in the eye, and swelling around the eye. It has been shown that combination of cyclosporine and corticosteroids lowers the risks of these side effects.

Therefore, the therapeutic agent may be a cyclosporine. Preferably, the pharmaceutical composition according to the present invention is administered prior to administration of cyclosporine, for example, 2 days, 5 days, or 1 week before administration of the cyclosporine.

IV—Pharmaceutical Packs or Kits

In another aspect, the present invention relates to pharmaceutical packs or kits. A pharmaceutical pack or kit according to the present invention comprises one or more containers (e.g., vials, ampoules, test tubes, flasks or bottles) containing one or more ingredients of an inventive composition, allowing administration of the composition to a subject. Such containers may be made of glass, plastic materials, resins, and the like. They may be transparent or, alternatively, they may be colored or opaque to prevent or reduce the risk that active ingredients be directly exposed to light. In certain embodiments, a container is in a form that allows for administration of a controlled volume (e.g., a drop) of an inventive composition. In other embodiments, a container comprises a system (e.g., a dropper) allowing administration of a controlled volume of an inventive composition.

Different ingredients of a pharmaceutical pack or kit may be supplied in a liquid form or in a solid form (e.g., lyophilized). Each ingredient will generally be suitable as aliquoted in its respective container or provided in a concentrated form. Pharmaceutical packs or kits may include media for the reconstitution of lyophilized ingredients. Individual containers of a kit will preferably be maintained in close confinement for commercial sale.

In certain embodiments, a pharmaceutical pack or kit includes one or more additional approved therapeutic agents as described above. Optionally associated with such container(s) can be a notice or package insert in the form prescribed by a governmental agency regulating the manufacture, use or sale of pharmaceutical or biological products, which notice reflects approval by the agency of manufacture, use or sale for human administration. The notice or package insert may contain instructions for use of a pharmaceutical composition according to methods disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Dexamethasone Palmitate Topical Emulsion at 0.16%

The following table (Table 1) shows the composition of a Dexamethasone palmitate (DP) topical emulsion according to the present invention.

TABLE 1

| Composition | % w/w |
|---|---|
| Medium chain triglycerides | 2 |
| Tyloxapol | 0.1 |
| Dexamethasone palmitate | 0.16 |
| Cetalkonium chloride | 0.005 |
| Glycerin | 2.25 |
| Water for injection | 95.485 |

Table 2 presents the specifications of the Dexamethasone palmitate (DP) topical emulsion.

TABLE 2

| Test | Value |
|---|---|
| Appearance | Milky white solution |
| pH | 6.05 |
| Osmolality | 268 mosmol/kg |
| Mean oil droplets size | 198 nm |
| Zeta potential | Positive (+41.0 mV) |
| Dexamethasone palmitate assay | 0.16181% w/w (101.1% of claimed value) |

Example 2

Dexamethasone Palmitate Topical Emulsion at 0.16% Combined with Cyclosporine A at 0.05%

Table 3 shows the composition of a Dexamethasone palmitate (DP) topical emulsion comprising cyclosporine A.

TABLE 3

| Composition | % w/w |
|---|---|
| Medium chain triglycerides | 2 |
| Tyloxapol | 0.1 |
| Dexamethasone palmitate | 0.16 |
| Cyclosporine A | 0.05 |
| Cetalkonium chloride | 0.005 |
| Glycerin | 2.25 |
| Water for injection | 95.435 |

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

The invention claimed is:

1. A pharmaceutical composition comprising an effective amount of a corticosteroid prodrug selected from the group consisting of dexamethasone, physiologically acceptable salts thereof, esters thereof, or any combinations thereof and at least one pharmaceutically acceptable carrier, wherein the pharmaceutically acceptable carrier is a cationic emulsion comprising medium chain triglyceride and quaternary ammonium compounds, and wherein the pharmaceutical composition is formulated for topical administration to the surface of the eye, such that administration of the pharmaceutical composition to a subject's eye surface results in insignificant penetration of the corticosteroid prodrug or corticosteroid or both inside the eye.

2. The pharmaceutical composition according to claim 1, wherein the corticosteroid prodrug comprises a lipophilic long chain ester of a dexamethasone, wherein said lipophilic long chain is selected from the group consisting of linear alkyls, branched alkyls, linear alkenyls, and branched alkenyls, wherein alkyls and alkenyls comprise 12, 14, 16, 18, or more carbon atoms.

3. The pharmaceutical composition according to claim 1, wherein the corticosteroid prodrug is dexamethasone myristate, dexamethasone laurate or dexamethasone caprate.

4. The pharmaceutical composition according to claim 1, wherein the pharmaceutical composition is formulated using an oily carrier.

5. The pharmaceutical composition according to claim 1, wherein the corticosteroid prodrug is converted to dexamethasone at the surface of the eye by enzymatic cleavage.

6. The pharmaceutical composition according to claim 1, wherein the pharmaceutically acceptable carrier or excipient is a member of the group consisting of antioxidant, viscosifying agent, preservative, pH adjusting agent, buffering agent, osmotic agent, chelating agent, penetration enhancing agent, and any combination thereof.

7. The pharmaceutical composition according to claim 1 further comprising at least one additional pharmaceutically active substance, preferably selected from the group consisting of an analgesic, an anesthetic, a haemostatic agent, an antimicrobial agent, an antibacterial agent, an antiviral agent, an antifungal agent, an antibiotic, an anti-inflammatory agent, an antioxidant, an antiseptic agent, an antihistamine agent, an antipruritic agent, an antipyretic agent, an immunostimulating agent, a dermatological agent, a anti-cancer agent, and any combination thereof.

8. The pharmaceutical composition of claim 7, wherein the additional pharmaceutical active substance is a cyclosporine.

9. The pharmaceutical composition according to claim 1, wherein the corticosteroid prodrug comprises a lipophilic long chain ester of dexamethasone, wherein said lipophilic long chain is selected from the group consisting of linear alkyls, branched alkyls, linear alkenyls, and branched alkenyls, wherein alkyls and alkenyls comprise 12, 14, 16, 18, or more carbon atoms.

* * * * *